United States Patent [19]

Masuzawa et al.

[11] Patent Number: 4,749,789

[45] Date of Patent: Jun. 7, 1988

[54] PROCESS FOR THE MANUFACTURE OF SPIRO-LINKED PYRROLIDINE 2,5-DIONES

[75] Inventors: Kuniyoshi Masuzawa, Koga; Kyuya Okamura, Ohmiya; Shizuyoshi Fujimori, Tochigi; Susumu Kinoshita; Hiroshi Matsukubo, both of Okaya, all of Japan

[73] Assignee: Kyorin Pharmaceutical Co., Ltd., Tokyo, Japan

[21] Appl. No.: 72,004

[22] Filed: Jul. 10, 1987

[30] Foreign Application Priority Data

Jul. 11, 1986 [JP] Japan ................ 61-161789

[51] Int. Cl.$^4$ ................ C07D 279/10; C07D 295/08; C07D 241/00
[52] U.S. Cl. ................ 544/6; 544/70; 544/230; 546/15
[58] Field of Search ............... 544/6, 70, 230; 546/15

[56] References Cited

U.S. PATENT DOCUMENTS 4,443,465 4/1984 Brittain et al. ............... 546/15
4,593,092 6/1986 Irikura et al. ............... 546/15

FOREIGN PATENT DOCUMENTS 1233684 10/1986 Japan ............... 546/15

OTHER PUBLICATIONS

Takagi et al., Chem. Abstracts. vol. 104, 5884s (1986).

*Primary Examiner*—Richard A. Schwartz
*Assistant Examiner*—J. Richter
*Attorney, Agent, or Firm*—Oblon, Fisher, Spivak, McClelland & Maier

[57] ABSTRACT

This invention relates to novel processes for the manufacture of spiro-linked pyrrolidine-2,5-diones of the formula;

which have a potent inhibitory activity on aldose reductase and are useful for reduction and prevention of chronic diabetic complications.

The invented processes are useful as improved and convenient method for a large scale manufacture.

3 Claims, No Drawings

PROCESS FOR THE MANUFACTURE OF SPIRO-LINKED PYRROLIDINE 2,5-DIONES

DETAILED DESCRIPTION OF THE INVENTION

This invention relates to novel processes for the manufacture of spiro-linked pyrrolidine-2,5-diones having a potent inhibitory activity on aldose reductase and which are useful for reduction and prevention of chronic diabetic complications.

In more detail, the invention relates to processes for the manufacture of spiro-linked pyrrolidine-2,5-diones represented by the formula;

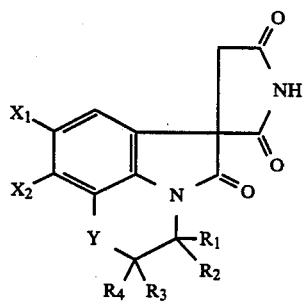
(I)

wherein $X_1$ and $X_2$ each independently represents a hydrogen atom, a halogen atom, a lower alkyl group or a lower alkoxy group; Y is a methylene group, an oxygen atom or a sulfur atom; $R_1$, $R_2$, $R_3$ and $R_4$ each independently represents a hydrogen atom, a lower alkyl group or forming a benzene ring together with their adjacent carbon atoms.

We have already discovered that spiro-linked pyrrolidine-2,5-diones of formula (I) possess potent aldose reductase inhibitory activities and are useful for reduction and prevention of chronic diabetic complications such as cataracts, neuropathy, nephropathy or retinopathy (Japan Kokai No. JP 60-142984; U.S. Pat. No. 4,593,092).

The process for preparing the compounds of formula (I) described in Japan Kokai No. JP 61-142984 (hereinafter called as the former method) is cited in below scheme.

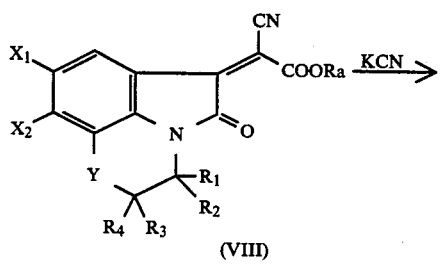
(VIII)

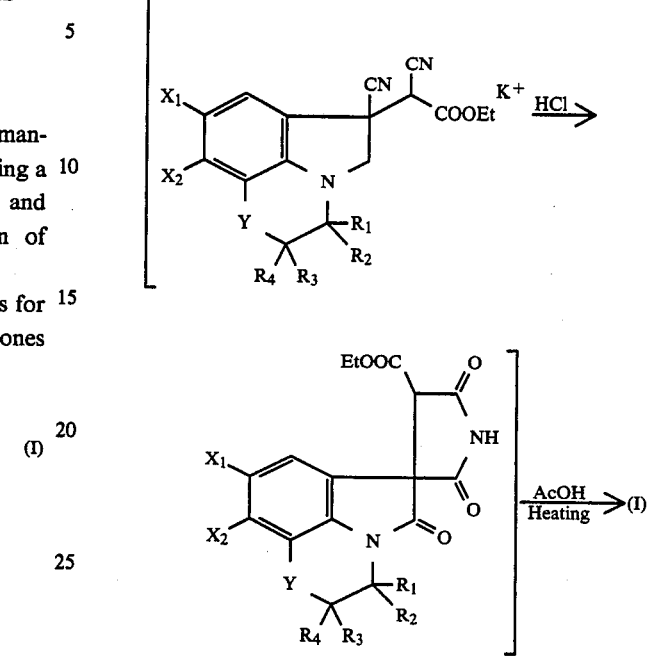

Thus the compounds of formula (I) are prepared by the addition of inorganic cyanide to the compounds of formula (VIII), wherein $X_1$, $X_2$, Y, $R_1$, $R_2$, $R_3$ and $R_4$ have the meanings defined above, and then by the decarboxylation on heating in acidic media after intramolecular cyclization in the presence of hydrogen chloride.

Defects of the former method for the mass production of the compounds of formula (I) are with perilous operation due to treating a large amount of inorganic cyanide. In addition, very expensive management is needed to prevent pollution due to disposition of a large amount of the wastes containing cyanides.

Furthermore at the next cyclocondensation step under treatment with hydrogen chloride, gaseous hydrogen cyanide is generated from the residual inorganic cyanides so that it is difficult to maintain operators safety. Then if such problems had not been resolved, it is unable to perform the mass production of the compounds of formula (I).

The present invention is aimed to provide the safe process for manufacture of the compounds of formula (I) without use of inorganic cyanides.

As a result of our continuous and zealous studies for overcoming defects of the former method, we have now completed this invention through the discovering of novel processes without using inorganic cyanides for the preparation of spiro-linked pyrrolidine-2,5-diones of formula;

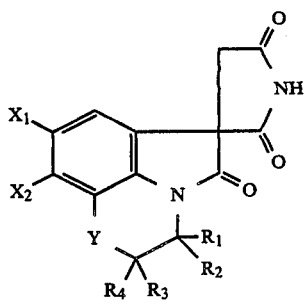

(I)

wherein $X_1$ and $X_2$ each independently represents a hydrogen atom, a halogen atom, a lower alkyl group or a lower alkoxy group; Y is a methylene group, an oxygen atom or a sulfur atom; $R_1$, $R_2$, $R_3$ and $R_4$ each independently represents a hydrogen atom, a lower alkyl group or forming a benzene ring together with their adjacent carbon atoms.

More specifically in the compounds of formula (I), the term "lower alkyl" as used in $X_1$, $X_2$, $R_1$, $R_2$, $R_3$ and $R_4$ means straight or branched hydrocarbons having 1 to 3 carbon atoms, such as a methyl, ethyl, n-propyl or isopropyl group. The term "lower alkoxy" as used in $X_1$ and $X_2$ means alkoxy groups having 1 to 3 carbon atoms, such as a methoxy, ethoxy, n-propoxy or isopropoxy group. The term "halogen atom" as used in $X_1$ and $X_2$ means a fluorine, chlorine, bromine or iodine atom. Y means a methylene group, an oxygen or sulfur atom. When $R_1$, $R_2$, $R_3$ and $R_4$ form a ring together with their adjacent carbon atoms, the ring means a benzene ring.

The compounds of formula (I) can be prepared through the novel process shown below. Thereby, $X_1$, $X_2$, Y, $R_1$, $R_2$, $R_3$ and $R_4$ indicate arbitrary ones among those described above, unless otherwise stated.

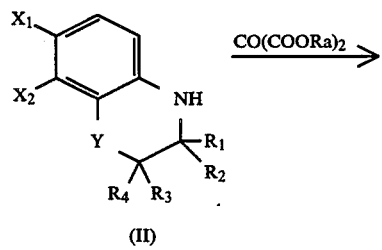

(II)

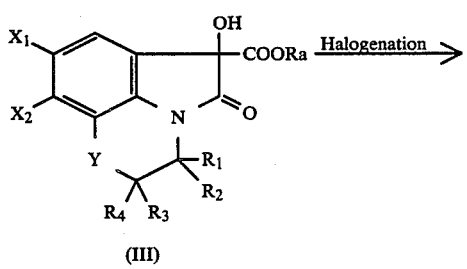

(III)

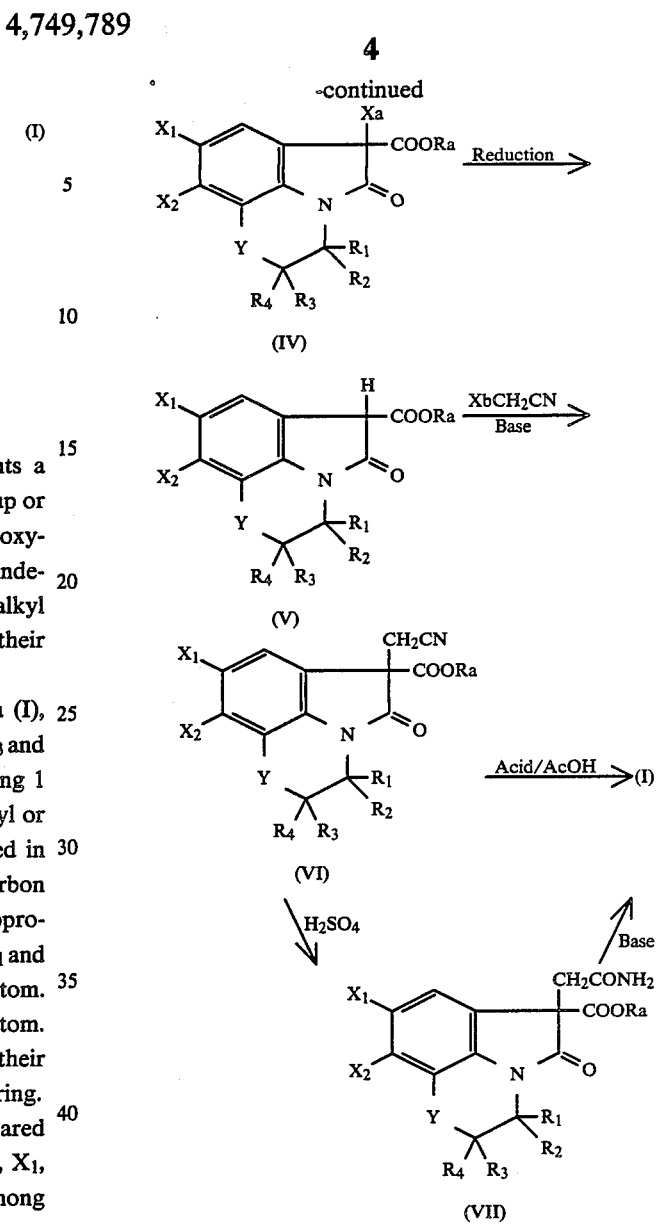

(IV)

(V)

(VI)

(VII)

The starting materials of formula (III), wherein Ra is a lower alkyl group, can be prepared by a reaction of the condensed cyclic amines of formula (II) with commercially available dialkyl ketomalonates or those monohydrates in such solvent as alkanoic acids. Whereby, the compounds of formula (II) are well known in the art or conventionally prepared. Ordinarily, acetic acid is used as a solvent and the equivalent or slightly excess molar diethyl ketomalonate is taken. The reaction of this step is completed within 10 to 30 minutes under reflux. Subsequently, the product can be obtained as a solid or crystals when the reaction mixture is diluted with water and neutralized. Although the isolation and purification may be conducted by the recrystallization from usual solvent such as alkanols, the product can be used only after dried without purification.

Next, the compounds of formula (IV), wherein Xa is a halogen atom, are prepared by replacing the hydroxide moiety of the compounds of formula (III) with a halogen atom. The halogenization may be carried out using excess molar halogeno hydrides, thionyl halides or phosphorous halides at a temperature range of 20° to 120° C., in a suitable solvent or without solvent. The reaction time is ordinarily required for 1 to 5 hours. The product can be obtained as a solid or crystals by evaporation of the excess reagent or solvent, in some cases by pouring on ice gradually. Although the purification is carried out with the recrystallization from usual solvent such as alkanols or carbon tetrachloride, the product can be used without purification for the next step only after washed well with water and dried.

Next, the compounds of formula (V) can be obtained by the reductive dehalogenation of the compounds of formula (IV). The reduction may be performed by the hydrogenation in the presence of palladium carbon in appropriate solvent such as tetrahydrofuran, ethyl acetate or ethanol, and carried out using metal such as zinc, tin or those halides in acetic acid or diluted hydrochloric acid, or using the complex hydride such as sodium borohydride in aqueous solvents at a temperature range 20° to 50° C. In same cases, the compounds of formula (V) can be prepared by treatment with active methylene donors such as diethyl malonate, ethyl cyanoacetate or ethyl acetoacetate in a polar solvent such as dimethylformamide in the presence of a base.

Alternatively, the reductive dehalogenation with ionic iodine is favorable for preparing the compounds of formula (V), conveniently and in high yields. In this case, the reduction is carried out with adding an aqueous solution of 5 to 10 fold molar sodium iodide or potassium iodide in alkanoic acid and then adding of saturated alkali sulfite in water. This reaction is completed within 15 to 30 minutes and then the product can be usually obtained as crystals by adding water. Its purification procedure should be done quickly because of the possibility of conversion to enolic form, though the recrystallization may be performed ordinarily from usual solvent such as alkanols. Advantageously, the product can be used for next step without recrystallizations.

The compounds of formula (VI) can be prepared by adding a halogeno acetonitrile such as chloroacetonitrile or bromoacetonitrile to the compounds of formula (V) in the presence of a base. The available base may be alkali metal alcoholates, alkali metals, alkali metal hydrides or alkali metal amides, and especially sodium hydride may be used to advantage in dimethylformamide as a solvent. The reaction can be carried out in a temperature range 20° to 80° C. and may be completed within 3 to 8 hours usually.

After completion of the reaction, the product is precipitated as viscous oil or solid by diluting reaction mixtures with water and followed by acidification, then extracted with such solvent as ethyl acetate, when an aquatic solvent is used. When a non-aquatic solvent used, the product is extracted directly after addition of water and acidification. The residual solid can be recrystallized from usual solvent such as cyclohexane or carbon tetrachloride ordinarily.

Finally, the spiro-linked pyrrolidine-2,5-diones of formula (I) can be obtained by refluxing of the compounds of formula (VI) for 4 to 6 hours in alkanoic acid such as acetic acid in the presence of catalytic sulfuric acid or polyphosphoric acid. The reaction may be carried out in only acetic acid under reflux and proceeds advantageously by the catalytic addition of concentrated sulfuric acid or polyphosphoric acid by 2 to 20% of proportion. Then the reaction mixture is poured into water and the resultant product can be collected as crystals. Thus, the compounds of formula (I) can be prepared in good purity after recrystallization from such solvent as acetic acid.

The process for preparation of compounds of formula (I) through the compounds of formula (VI) is conveniently preferable to the former method preparing by the decarboxylation.

Moreover, the process for preparation of the compounds of formula (I) through the compounds of formula (VI), in more mild condition as stated below, can be included in this invention. The compounds of formula (VII) can be prepared by treating the compounds of formula (VI) with concentrated sulfuric acid. This reaction may be conducted at a room temperature and completed in 1 to 2 hours. Afterward the product may be yielded as crystals quantitatively from the reaction mixture when poured into ice-water gradually. The purification may be carried out with recrystallization from alkanols, and especially the product can be used to the next step without recrystallizations.

The compounds of formula (VII) thus obtained are dissolved in an equimolar aqueous base such as sodium or potassium hydroxide, or an equimolar alcoholic alkali metal hydroxide to afford spiro-linked pyrrolidine-2,5-diones of formula (I) in high yield. This reaction is usually completed within 20 to 60 minutes. After dilution with cold water and acidification, the product can be obtained as crystals without by-products conveniently. This alternative process is favorable to compounds having a unstable substituent, since heating is not required.

Moreover, the compounds represented by the formula from (III) to (VII) have not been known yet.

Thus obtained compounds of formula (I) all possess one to two asymmetric carbon atoms, namely at least the spiro carbon atom at position 3 of the pyrrolidine ring. Therefore they exist in one or more racemic forms, it is naturally to say that this invention encompasses the process for the preparation in racemic or any optically-active forms.

Above stated processes for the preparation of compounds of formula (I) bring on safety in usual facilities for industrial manufacture since they does not require use of inorganic cyanides. Moreover, this invented methods are superior to the former method because of shortness of processes and high yield. In particularly, the final step is simplified since it does not require the decarboxylation. And the alternative method is favorable for providing the excellent pure products in good yield by controlling the side reaction under mild condition without heating.

Now the processes in this invention would be stated below. It will be understood that the invention is not limited to the specific details of these examples.

EXAMPLE 1

Ethyl 8-chloro-2,3-dihydro-6-hydroxy-5-oxopyrrolo[1,2,3-de]-1,4-benzoxazine-6-carboxylate 7-Chloro-3,4-dihydro-2H-1,4-benzoxazine (Japan Kokai JP No. 61-152984, U.S. Pat. No. 4,593,092) (19.77 g. 0.116 mol) was dissolved in 74 ml of acetic acid and to which diethyl ketomalonate 20.2 g (0.116 mol) was added dropwise at a room temperature. Then after refluxing for 20 minutes, the mixture was stand for overnight. After pouring into 500 ml of ice, ammonium carbonate was added to the solution. The resultant crystalline solid was collected by filtration, washed with water and dried to yield pale orange powders quantitatively. Recrystallization from ethanol afforded 26.67 g (77.3%) of the title compound as pale yellow prisms, mp 186°–187° C.

NMR (d$_6$-DMSO: ppm); 1.11 (t, 3H, CH$_3$), 3.80 (t, 2H, CH$_2$N), 4.14 (t, 2H, ester CH$_2$), 4.32 (t, 2H, OCH$_2$), 6.92 and 7.06 (dd, 2H, aromatic-H), 7.32 (s, 1H, OH, D$_2$O exchangeable).

Analysis (%) for C$_{13}$H$_{12}$ClNO$_5$, Calcd. (Found): C, 52.45 (52.58); H, 4.06 (3.98); N, 4.71 (4.63).

EXAMPLE 2

Ethyl 6,8-dichloro-2,3-dihydro-5-oxopyrrolo[1,2,3-de]-1,4-benzoxazine-6-carboxylate The compound of example 1 (26.67 g, 0.09 mol) was refluxed in 53 ml of thionyl chloride for 3 hours. After excess thionyl chloride was evaporated as much as possible, the resultant suspension was poured into 800 ml of ice-water with stirring vigorously. The depositing solid was filtered off, washed well with water, and dried to give yellow powders quantitatively. Recrystallization from ethanol afforded 24.8 g (87.4%) of the title compound as pale yellow fine needles, mp 147°–148° C.

NMR (d$_6$-DMSO: ppm); 1.17 (t, 3H, CH$_3$), 3.89 (t, 2H, CH$_2$N), 4.24 (q, 2H, ester CH$_2$), 4.36 (t, 2H, OCH$_2$), 7.15 (m, 2H, aromatic-H).

Analysis (%) for C$_{13}$H$_{11}$Cl$_2$NO$_4$, Calcd. (Found): C, 49.39 (49.37); H, 3.51 (3.42); N, 4.43 (4.41).

EXAMPLE 3

Ethyl 8-chloro-2,3-dihydro-5-oxopyrrolo[1,2,3-de]-1,4-benzoxazine-6-carboxylate

Method A

The compound of example 2 (12.65 g, 0.04 mol) was suspended in 120 ml of acetic acid, and to which 40 ml of 5M aqueous solution of potassium iodide was added dropwise. After stirring for 15 minutes at room temperature, the brown iodine color was discharged by the dropwise addition of saturated aqueous sodium sulfite solution (40 ml). After stirring for more 15 minutes, the reaction mixture was poured into 700 ml of water. The precipitate was collected by filtration, washed well with water and dried to afford 10.89 g (91.8%) of the title compound as colorless needles, mp 103.5°–104.5° C. Recrystallization from ethanol gave the colorless needles which melted at 102°–103° C.

IR (KBr): CO; 1675, 1610 (cm$^{-1}$).

Mass spectra (70 ev): m/e 281 (M$^+$), 235 (M$^+$-OC$_2$H$_5$).

Analysis (%) for C$_{13}$H$_{12}$ClNO$_4$, Calcd. (Found): C, 55.42 (55.26); H, 4.30 (4.21); N, 5.00 (4.98).

Method B

Fifty-five percent oil dispersed sodium hydride (0.79 g, 0.018 mol) was washed with n-hexane and suspended in anhydrous dimethylformamide (50 ml). To which diethyl malonate 2.64 g (0.017 mol) was added dropwise at room temperature with stirring. The compound of example 2 (4.74 g, 0.015 mol) was added to the mixture. After stirring for 2.5 hours, the reaction mixture was poured into 200 ml of water and then acidified with 6N hydrochloric acid immediately. The precipitated solid was collected by filtration, washed well with water and recrystallized from ethanol (25 ml) to afford 2.23 g (52.9%) of the title compound, mp 105°–106° C.

Analysis (%) for C$_{13}$H$_{12}$ClNO$_4$, Calcd. (Found): C, 55.42 (55.20); H, 4.30 (4.20); N, 5.00 (4.92).

Spectrometric agreement between the product by method A and method B was obtained.

EXAMPLE 4

Ethyl 8-chloro-6-cyanomethyl-2,3-dihydro-5-oxopyrrolo[1,2,3-de]-1,4-benzoxazine-6-carboxylate

Method A

Fifty-five percent sodium hydride (0.523 g, 0.012 mol) was washed with n-hexane and suspended in 40 ml of anhydrous dimethylformamide. To which the compound of example 3 (2.82 g, 0.01 mol) was added gradually at room temperature with stirring. A sufficient amount of bromoacetonitrile was added to the stirred mixture. After stirring for one hour and then at 50° C. for 2 hours, the reaction mixture was poured into 300 ml of water. After treating with 6N hydrochloric acid, the separated viscous oil was extracted with ethyl acetate (50 ml), washed with water and dried. The concentrated viscous residue was triturated with a little ether to give a solid, then collected by filtration and dried to afford to 2.64 g (82.2%) of the title compound as brownish powders. Recrystallization with carbon tetrachloride gave 2.13 g (65.3%) of colorless prisms, mp 134°–135° C.

NMR (CDCl$_3$: ppm); 1.22 (t, 3H, CH$_3$), 3.20 (q, AB type, J=16.9 Hz, 2H, CH$_2$CN), 3.92 (t, 2H, NCH$_2$), 4.08–4.39 (m, 4H, ester-CH$_2$ and OCH$_2$), 7.00 (s, 2H, aromatic-H).

Analysis (%) for C$_{15}$H$_{13}$ClN$_2$O$_4$, Calcd. (Found): C, 56.17 (55.98); H, 4.08 (4.04); N, 8.74 (8.69).

Method B

By using of chloroacetonitrile instead of bromo derivative the reaction was carried out by the same treatment described in part A, with stirring at 80° C. for 4.5 hours after addition of the reagent. There was obtained 1.82 g (56.7%) of colorless fine needles after recrystallization, mp 130°–131° C., which are superimposable with spectra data of method A product.

EXAMPLE 5

8'-Chloro-2',3'-dihydrospiro[pyrrolidine-3,6'(5'H)-pyrrolo-[1,2,3-de][1,4]benzoxazine]-2,5,5'-trione The compound of example 4 (1.6 g, 0.005 mol) was refluxed in a mixture of acetic acid (10 ml) and concentrated sulfuric acid (0.5 ml) for 4 hours. After pouring into 100 ml of water, the precipitate was collected by filtration, washed well with water and dried to afford 1.12 g (76.5%) of the title compound. There was obtained 0.81 g (55.3%) of colorless prisms after recrystallization from acetic acid, mp 268°–269° C.

Analysis (%) for C$_{13}$H$_9$ClN$_2$O$_4$, Calcd. (Found): C, 53.34 (53.20); H, 3.10 (3.11); N, 9.57 (9.42).

Thus obtained compound was identified with the compound described in prior art (Japan Kokai No. JP 60-142984, U.S. Pat. No. 4,593,092) by comparison of analytical data.

EXAMPLE 6

Ethyl 6-carbamoylmethyl-8-chloro-2,3-dihydro-5-oxopyrrolo-[1,2,3-de]-1,4-benzoxazine-6-carboxylate The compound of example 4 (3.71 g, 0.012 mol) was dissolved in 20 ml of concentrated sulfuric acid and the mixture was stirred for 1.5 hours at room temperature. After pouring into 250 ml of ice-cold water, the precipitate was collected by filtration, washed well with water and dried to give 3.85 g (98.2%) of the title compound as colorless prisms, mp 227°–229° C.

Recrystallization from ethanol afforded colorless prisms melted at 224°–226° C.

NMR ($d_6$-DMSO: ppm); 1.10 (t, 3H, $CH_3$), 3.05 (q, AB type, J=16.2 Hz, $CH_2CO$), 3.78 (m, 2H, $CH_2N$) 4.07 (q, 2H, ester $CH_2$), 4.29 (t, 2H, $OCH_2$), 6.84 and 7.43 (bs, 2H, $OCH_2$), 6.96 and 7.13 (dd, J=1.76 Hz, 2H, aromatic-H).

Analysis (%) for $C_{15}H_{15}ClN_2O_5$, Calcd. (Found): C, 53.18 (52.26); H, 4.46 (4.43); N, 8.27 (8.23).

EXAMPLE 7

8'-Chloro-2',3'-dihydrospiro[pyrrolidine-3,6'(5'H)-pyrrolo-[1,2,3-de][1,4]benzoxazine]-2,5,5'-trione The compound of example 6 (1.69 g, 0.005 mol) was suspended in 25 ml of ethanol and to which 0.5N sodium hydroxide (12 ml, 0.006 mol) was added dropwise at room temperature. After the compound was dissolved to clear solution, stirring continued for more 20 minutes and then the reaction mixture was poured in 250 ml of cold water. After acidifying with 6N hydrochloric acid, deposited solid was collected by filtration, washed well with water and dried. There was obtained the title compound (1.29 g, 88.2%) as colorless powders, mp 226.5°–268° C.

Analysis (%) for $C_{13}H_9ClN_2O_4$, Calcd. (Found): C, 53.34 (53.31); H, 3.10 (3.18); N, 9.57 (9.49).

In addition, recrystallization from acetic acid afforded 0.9 g (61.5%) of the compound as colorless prisms, mp 268°–269° C.

Analysis (%) for $C_{13}H_9ClN_2O_4$, Calcd. (Found): C, 53.34 (53.34); H, 3.10 (3.10); N, 9.57 (9.48).

By this procedure, even a crude mass scarcely contained impurity as shown by that elemental analysis.

Besides thus obtained compound was identified with the ones prepared in example 5 and by the conventional method in all respects.

What is claimed is:

1. A process for the synthesis of a spiro-linked pyrrolidine-2,5-dione of the formula:

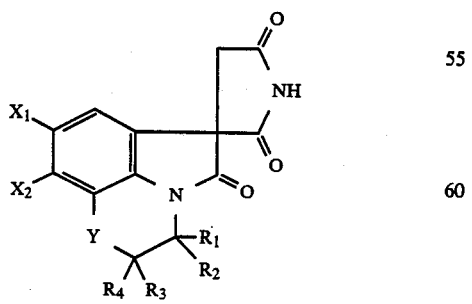

wherein $X_1$ and $X_2$ each independently represent a hydrogen atom, a halogen atom, a lower alkyl group or an alkoxy group; Y is a methylene group, an oxygen atom or a sulfur atom; $R_1$, $R_2$, $R_3$ and $R_4$ each independently represent a hydrogen atom, a lower alkyl group or the carbon atoms of adjacent groups together form a benzene ring, comprising:

(a) reacting ketomalonic acid or monohydrate thereof with a compound of the formula:

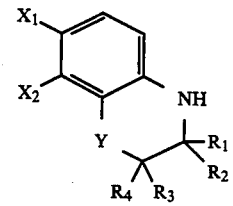

wherein $X_1$, $X_2$, Y, $R_1$, $R_2$, $R_3$ and $R_4$ have the above-stated meaning, (b) halogenizing the product obtained from step (a) of the formula:

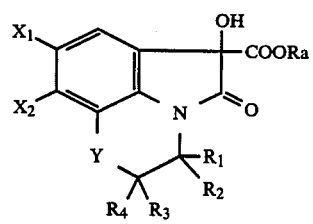

wherein Ra, $X_1$, $X_2$, Y, $R_1$, $R_2$, $R_3$ and $R_4$ each have the above-stated meanings;

(c) reductively dehalogenating the compound obtained from step (b) of the formula:

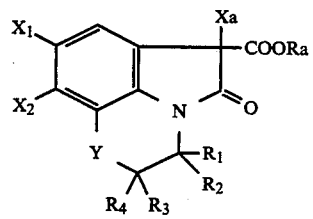

wherein Xa is a halogen atom and Ra, $X_1$, $X_2$, $R_1$, $R_2$, $R_3$ and $R_4$ each have the meanings stated above;

(d) reacting monohalogenoacetonitrile in the presence of a base with the compound obtained from step (c) of the formula:

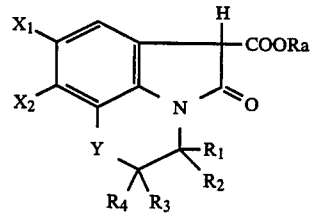

wherein Ra, $X_1$, $X_2$, Y, $R_1$, $R_2$, $R_3$ and $R_4$ each have the above-stated meanings; and heating the compound obtained from step (d) of the formula:

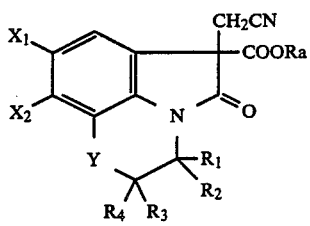

wherein Ra, $X_1$, $X_2$, Y, $R_1$, $R_2$, $R_3$ and $R_4$ each have the above-stated meanings.

2. A process for the synthesis of a spiro-linked pyrrolidine-2,5-dione of the formula:

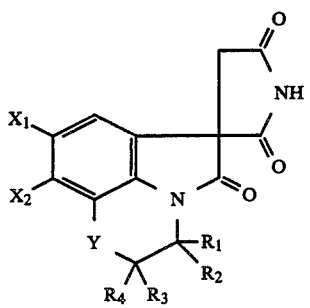

wherein $X_1$ and $X_2$ each independently represent a hydrogen atom, a halogen atom, a lower alkyl group or a lower alkoxy group; Y is a methylene group, an oxygen atom or a sulfur atom; $R_1$, $R_2$, $R_3$ and $R_4$ each independently represent a hydrogen atom, a lower alkyl group or the carbon atoms of adjacent groups together form a benzene ring, comprising:
cyclizing a compound of the formula:

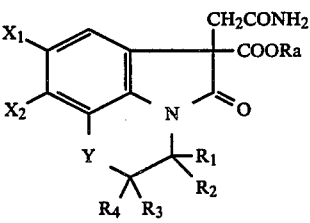

wherein Ra is a lower alkyl group and $X_1$, $X_2$, Y, $R_1$, $R_2$, $R_3$ and $R_4$ each have the above-stated meanings, in the presence of a base.

3. A process for the synthesis of a spiro-linked pyrrolidine-2,5-dione of the formula:

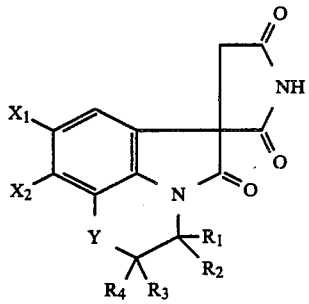

wherein Ra, $X_1$, $X_2$, Y, $R_1$, $R_2$, $R_3$ and $R_4$ each have the meanings stated in any of the above claims, comprising:
(a) hydrating, in an acid medium, a compound of the formula:

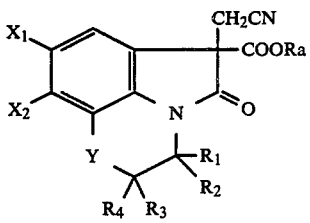

wherein Ra, $X_1$, $X_2$, Y, $R_1$, $R_2$, $R_3$ and $R_4$ each have the above-stated meanings; and
(b) cyclizing the product obtained from step (a) of the formula:

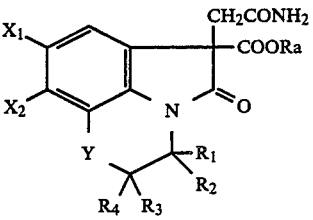

wherein Ra, $X_1$, $X_2$, Y, $R_1$, $R_2$, $R_3$ and $R_4$ each have the above-stated meanings.

* * * * *